(12) United States Patent
Guidotti et al.

(10) Patent No.: US 7,431,715 B2
(45) Date of Patent: Oct. 7, 2008

(54) ABSORBENT ARTICLE

(75) Inventors: Ted Guidotti, Göteborg (SE); Mikael Andersson, Göteborg (SE)

(73) Assignee: SCA Hygiene Products AB, Gothenburg (SE)

( * ) Notice: Subject to any disclaimer, the term of this patent is extended or adjusted under 35 U.S.C. 154(b) by 256 days.

(21) Appl. No.: 10/671,541

(22) Filed: Sep. 29, 2003

(65) Prior Publication Data

US 2004/0064119 A1   Apr. 1, 2004

Related U.S. Application Data

(60) Provisional application No. 60/413,764, filed on Sep. 27, 2002.

(51) Int. Cl.
*A61F 13/15* (2006.01)
(52) U.S. Cl. .............. 604/385.101; 604/378; 604/379; 604/380; 604/385.23
(58) Field of Classification Search .......... 604/385.101, 604/378–380, 385.23
See application file for complete search history.

(56) References Cited

U.S. PATENT DOCUMENTS

| | | | |
|---|---|---|---|
| 3,017,304 A | 1/1962 | Burgeni | |
| 3,860,003 A | 1/1975 | Buell | |
| 4,834,735 A * | 5/1989 | Alemany et al. | ............ 604/368 |
| 5,134,007 A * | 7/1992 | Reising et al. | ................. 428/78 |
| 5,348,547 A | 9/1994 | Payne et al. | |
| 5,986,167 A | 11/1999 | Arteman et al. | |
| 6,123,692 A * | 9/2000 | Guidotti et al. | ........ 604/385.01 |

FOREIGN PATENT DOCUMENTS

| | | |
|---|---|---|
| EP | 0 219 326 B1 | 4/1987 |
| EP | 1 035 818 B1 | 9/2000 |
| WO | 98/22067 A1 | 5/1998 |
| WO | 00/19955 A2 | 4/2000 |
| WO | 00/19955 A3 | 4/2000 |
| WO | 00/76446 A1 | 12/2000 |
| WO | 00/76447 A1 | 12/2000 |
| WO | 01/00129 A1 | 1/2001 |

* cited by examiner

*Primary Examiner*—Jacqueline F. Stephens
(74) *Attorney, Agent, or Firm*—Buchanan Ingersoll & Rooney, PC

(57) ABSTRACT

An absorbent article includes an absorbent core (4) including a fluid storage member (18), a fluid distribution layer (17) and a fluid receiving layer (16). The distribution layer (17) is disposed to extend in the crotch portion (7) and in at least a substantial portion of one of the waist portions (5 or 6) of the article and is absent in at least a substantial part of the opposite waist portion of the article so as to promote fluid flow from the crotch portion (7) towards the one waist portion (5 or 6). A fluid barrier (19) is arranged at or in close proximity to one transverse end edge of the fluid distribution layer (17), located in or adjacent the crotch portion (7) of the article, the fluid barrier (19) extending through at least a substantial part of the thickness of the layer.

13 Claims, 4 Drawing Sheets

ABSORBENT ARTICLE

CROSS-REFERENCE TO RELATED APPLICATIONS

This application claims the benefit under 35 U.S.C. § 119 (e) of U.S. provisional application No. 60/413,764 filed on Sep. 27, 2002, the entire content of which is incorporated by reference.

TECHNICAL FIELD OF THE INVENTION

The present invention refers to an absorbent article, such as a diaper, pant diaper, incontinence guard, sanitary napkin or the like. The article comprises an absorbent core including at least one fluid storage member and at least one fluid distribution layer overlapping and being in fluid contact with the fluid storage member.

BACKGROUND OF THE INVENTION

Absorbent articles of this kind are usually made rather thin as compared to their longitudinal and transverse extensions. In order to provide sufficient capacity for storing discharged body fluid, the absorbent material which is included in the article is spread over a large area, which for a diaper extends from the stomach of the user via the crotch region to the waist area on the back of the user.

When a user is standing or sitting the discharged urine ends up in the so called "wetting area", which is located in the crotch portion of the article, and to avoid local leakage near the wetting area it is important that the article is designed so that liquid is spread quickly over available absorption material. As the distance to the side edges of the article is small as compared to the longitudinal extension of the article, liquid distribution layers are often provided, which distribute liquid in the longitudinal direction of the article. At the same time measures are also often taken to prevent spreading of liquid in the transverse direction out of the article.

In an attempt to prevent lateral leakage, diapers are nowadays provided with so called leg elastics, which hold the side edges of the article in sealing contact against the body. Leg elastics of this kind are described in, for example U.S. Pat. No. 3,860,003. In order to further improve security against lateral leakage it is known to use upright leakage barriers on either side of the crotch region. Leakage barriers of this type are described in, for example EP 0 219 326 B1.

In order to spread liquid in the longitudinal direction of the article from the wetting area, which in substance is the lowest point of the article, liquid must be transported in an upward direction against the effect of gravity. This liquid distribution problem has occupied diaper manufacturers for several decades and a number of different types of wicking layers have been suggested in order to improve liquid distribution in the longitudinal direction.

U.S. Pat. No. 3,017,304 discloses a wicking layer made by wetting one side of an absorbent body of fluff pulp and subsequently compressing the absorbent body, wherein the compression leads to the formation of a compressed wicking layer on the wetted side of the absorbent body. In modern diapers the wicking layer is normally made of compressed chemical fluff pulp.

However no solution has yet been proposed, which provides a sufficiently effective liquid distribution in the longitudinal direction of the article in order to optimally utilize available absorption material. Diapers normally leak laterally long before all absorbent material located at a distance from the wetting area has been utilized. A better utilization of absorbent material in the article is important from economical viewpoint, but also for environmental reasons. If the absorbent material included in a diaper and the like can be better utilized, the amount of absorbent materials needed in the article can be reduced, leading to a smaller need for raw material and a reduction of the waste which originates from used diapers and the like.

One problem with known diapers or the like is that liquid does not spread sufficiently effectively against the force of gravity with the help of a wicking layer. Liquid accumulates in the lowest situated region of the diaper, which is constituted by the wetting area.

WO 00/19955 discloses an absorbent article having wicking barriers preventing radial wicking in the plane of the article and thus promotes central filling of the article with fluid and reduces the likelihood of leaks from the sides of the article.

In WO 00/76447 there is suggested to provide liquid impermeable portions at separate locations of overlapping parts of a wicking layer and liquid storage layers, so as to prevent the transfer of liquid from the wicking layer to the storage layers over said impermeable portions. The impermeable portions are arranged at either sides of a liquid receiving area, so that liquid acquired by said liquid receiving zone is spread in said wicking layer towards the rear and front portions of the article and at a certain distance from the liquid receiving zone is transferred into the storage layers.

However one problem that arises when the wearer, for example the baby, lies down on the stomach, is that the liquid will follow gravity down to the front part of the diaper. This means that the front part of the product gets saturated with liquid, while the back area usually goes on unutilised. The corresponding problem occurs when the wearer lies down on the back, at which the back area of the diaper gets saturated and the front area remains unutilised.

OBJECTS AND SUMMARY

One object of the present invention is to provide an absorbent article having improved liquid handling properties. A further object is to provide an absorbent article having improved security against leakage when the wearer lies down on the stomach or on the back. Still a further object is to provide an absorbent article enabling an improved utilization of the absorbent material in the article.

An absorbent article comprises an absorbent core including at least one fluid storage member, at least one fluid distribution layer overlapping and being in fluid contact with the fluid storage member and at least one fluid receiving layer arranged in at least the crotch area of the article in direct or indirect fluid contact with the fluid distribution layer and the fluid storage layer, said fluid storage layer, said fluid distribution layer and said fluid receiving layer each having longitudinal end edges that extend along the longitudinal direction and transverse end edges that extend along the transverse direction. At least one fluid barrier is arranged to extend in the transverse direction of the article. The fluid distribution layer is disposed to extend in the crotch portion and in at least a substantial portion of one of the waist portions of the article and is absent in at least a substantial part of the opposite waist portion of the article so as to promote fluid flow from the crotch portion towards said one waist portion. The fluid barrier is arranged at or in close proximity to one of the transverse end edges of the fluid receiving layer, located in or adjacent the crotch portion of the article, said fluid barrier extending through at least a substantial part of the thickness of said fluid receiving layer.

In one embodiment of the invention, intended for a wearer lying on the stomach, the at least one fluid storage layer is disposed in at least a substantial part of the front and rear portions of the article, that said fluid distribution layer is disposed in the crotch portion and at least a substantial part of rear portion of the article and is absent in at least a substantial part of the front portion of the article, and that the fluid barrier is arranged at or in close proximity to the transverse end edge of the fluid receiving layer facing the front portion of the article.

In one embodiment of the invention, the article is a diaper or pant diaper intended to be used by babies lying on their stomach.

In an alternative embodiment, intended for a wearer lying on the back, the at least one fluid storage layer is disposed in at least a substantial part of the front and rear portions of the article, said fluid distribution layer is disposed in at least a substantial part of the crotch and front portions of the article and is absent in at least a substantial part of the rear portion of the article and that the fluid barrier is arranged at or in close proximity to the transverse end edge of the fluid receiving layer facing the rear portion of the article.

In one embodiment, the fluid distribution layer is located between the fluid receiving layer and the fluid storage layer and the fluid barrier is arranged to extend a certain distance in between the fluid receiving layer and the fluid distribution layer.

In a further embodiment the fluid barrier member is arranged also to extend through at least a substantial part of the thickness of the fluid distribution layer at or in close proximity to one transverse end edge of said layer.

In one embodiment, the fluid distribution layer is located between the fluid receiving layer and the fluid storage layer and the fluid barrier is arranged to extend a certain distance in between the fluid distribution layer and the fluid storage layer.

According to another embodiment, the fluid distribution layer is located between the fluid receiving layer and the fluid storage layer and the fluid barrier is arranged to extend through the fluid storage layer.

According to still another embodiment, the fluid receiving layer is arranged in a recess between front and rear portions of a fluid storage layer, wherein the fluid distribution layer is arranged under the fluid receiving layer and the rear or the front portion of the fluid storage layer, and wherein the fluid barrier is arranged between the fluid receiving layer and the rear or the front portion of the fluid storage layer and to substantially cover the edge of the fluid distribution layer facing the front or the rear portion of the article.

The material in the fluid distribution layer should have a higher liquid affinity than the material in the liquid receiving layer so as to promote liquid transport from the liquid receiving layer to the fluid distribution layer. The material in the fluid storage layer should have a higher liquid affinity than the material in the fluid receiving layer and the fluid distribution layer so as to promote liquid transport from the fluid receiving layer and the fluid distribution layer to the fluid storage layer.

The fluid barrier is preferably made from a hydrophobic nonwoven material, a plastic film material, laminates thereof and/or a coating of a hydrophobic and/or liquid tight material on a carrier material and/or is constituted by an edge portion of the fluid distribution layer and or the fluid receiving layer respectively that has been modified by thermal, mechanical, chemical or other treatment so as to make it prevent or at least delay liquid penetration.

BRIEF DESCRIPTION OF THE DRAWINGS

Embodiments of the invention will below be described more in detail with reference to the accompanying drawings.

DETAILED DESCRIPTION OF THE PREFERRED EMBODIMENTS

The term "absorbent article" refers to products that are placed against the skin of the wearer to absorb and contain body exudates, like urine, faeces and menstrual fluid. The invention mainly refers to disposable absorbent articles, which means articles that are not intended to be laundered or otherwise restored or reused as an absorbent article after use. Examples of disposable absorbent articles include feminine hygiene products such as sanitary napkins, pantiliners and sanitary panties; diapers and pant diapers for infants and incontinent adults; incontinence pads; diaper inserts and the like.

Figure 1:
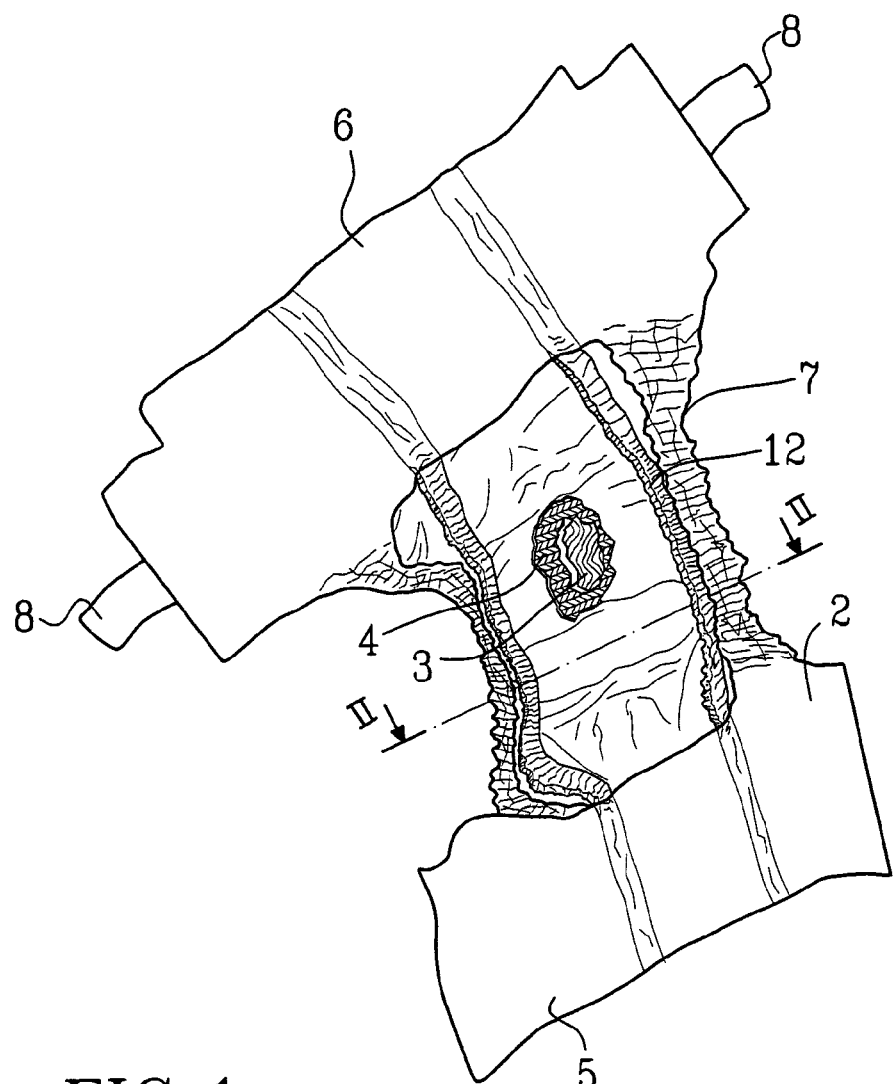
FIG. 1 is a perspective view of an absorbent article in the form of a diaper.

FIG. 1 shows an embodiment of a diaper 1 for an infant or an incontinent adult, said diaper typically comprises a chassis comprising a liquid permeable topsheet 2, a liquid impermeable backsheet 3 and an absorbent body 4 enclosed therebetween. The liquid permeable topsheet 2 can consist of a non-woven material, e.g., spunbonded, meltblown, carded, hydroentangled, wetlaid etc. Suitable nonwoven materials can be composed of natural fibers, such as woodpulp or cotton fibres, manmade fibres, such as polyester, polyethylene, polypropylene, viscose etc. or from a mixture of natural and manmade fibres. The topsheet material may further be composed of tow fibres, which may be bonded to each other in a bonding pattern, as, e.g., disclosed in EP-A-1 035 818. Further examples of topsheet materials are porous foams, apertured plastic films etc. The materials suited as topsheet materials should be soft and non-irritating to the skin and be readily penetrated by body fluid, e.g., urine or menstrual fluid.

The liquid impermeable backsheet 3 may consist of a thin plastic film, e.g., a polyethylene or polypropylene film, a nonwoven material coated with a liquid impervious material, a hydrophobic nonwoven material, which resists liquid penetration or laminates of plastic films and nonwoven materials. The backsheet material may be breathable so as to allow vapour to escape from the absorbent core, while still preventing liquids from passing through the backsheet material.

The topsheet 2 and the backsheet material 3 have a somewhat greater extension in the plane than the absorbent body 4 and extend outside the edges thereof. The layers 2 and 3 are connected to each other within the projecting portions thereof, e.g., by gluing or welding by heat or ultrasonic. The topsheet and/or the backsheet may further be attached to the absorbent core by any method known in the art, such as adhesive, heatbonding etc. The absorbent core may also be unattached to the topsheet and/or the backsheet.

The absorbent body 4 can be of any conventional kind. Examples of commonly occurring absorbent materials are cellulosic fluff pulp, tissue layers, highly absorbent polymers (so called superabsorbents), absorbent foam materials, absorbent nonwoven materials or the like. It is common to combine cellulosic fluff pulp with superabsorbents in an absorbent body. It is also common to have absorbent bodies comprising layers of different material with different properties with respect to liquid receiving capacity, liquid distribution capacity and storage capacity. The thin absorbent bodies, which are common in for example baby diapers and incontinence guards, often comprise a compressed mixed or layered structure of cellulosic fluff pulp and superabsorbent. The size and absorbent capacity of the absorbent core may be varied to be suited for different uses such as baby diapers, adult incontinence diapers and pads, pant diapers, pantiliners, sanitary napkins etc.

The diaper disclosed in FIG. 1 is intended to enclose the lower part of the wearer's trunk like a pair of absorbent pants. It comprises a front portion 5 intended during use to be worn on the front part of the user's body, a rear portion 6 intended during use to be worn on the rear part of the user's body, and a more narrow crotch portion 7 located between the front and rear portions and which is intended to be worn in the crotch part of the user between the legs. The front portion 5 is provided with a pair of adhesive tape tabs 8 or other type of attachment means such as hook-and-loop type fasteners.

Figure 2:
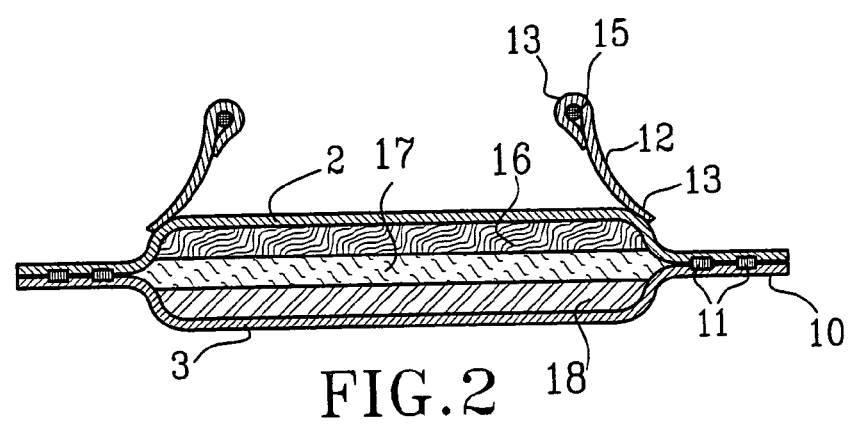
FIG. 2 is a transverse sectional view through the diaper.

The diaper comprises elasticised side flaps 10 forming leg openings. Elastification is provided by elastic members 11 secured between the topsheet and backsheet in the side flap region 10. The diaper disclosed in FIGS. 1 and 2 further comprises elastic barrier flaps 12 having a proximal edge 13 and a distal edge 14 and elastic member 15 spacing the distal edge 14 away from the topsheet. These barrier flaps 12 form leakage barriers and are at their proximal edges 13 secured to the topsheet 2 close to the lateral edges of the absorbent core 4 either in the area of the side flaps 10 or above the absorbent core 4.

The diaper may further comprise elasticised waist feature in the form of elastic members extending in the transverse direction of the article in the waist portion thereof.

In a further embodiment the diaper comprises belt portions attached to the rear portion of the diaper and intended to be fastened together around the waist of the wearer. Fastening means on the front part of the diaper are then attached to the outside of the belt to fasten together the diaper to the desired pantlike shape. An example of a belted diaper is shown in WO 01/00129.

It is however understood that the diaper described above and shown in the drawing only represents one non-limiting example and that the present invention is not limited thereto, but can be used in any type of absorbent articles as defined above.

Figure 3A:
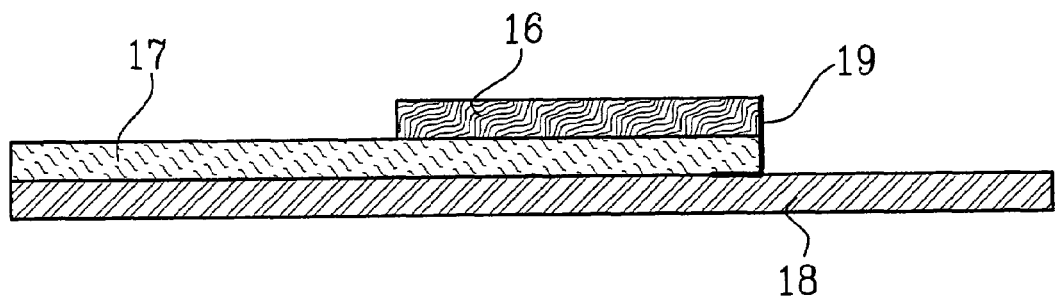
FIG. 3a is a longitudinal section through a first embodiment of an absorbent body according to the invention.
Figure 4:
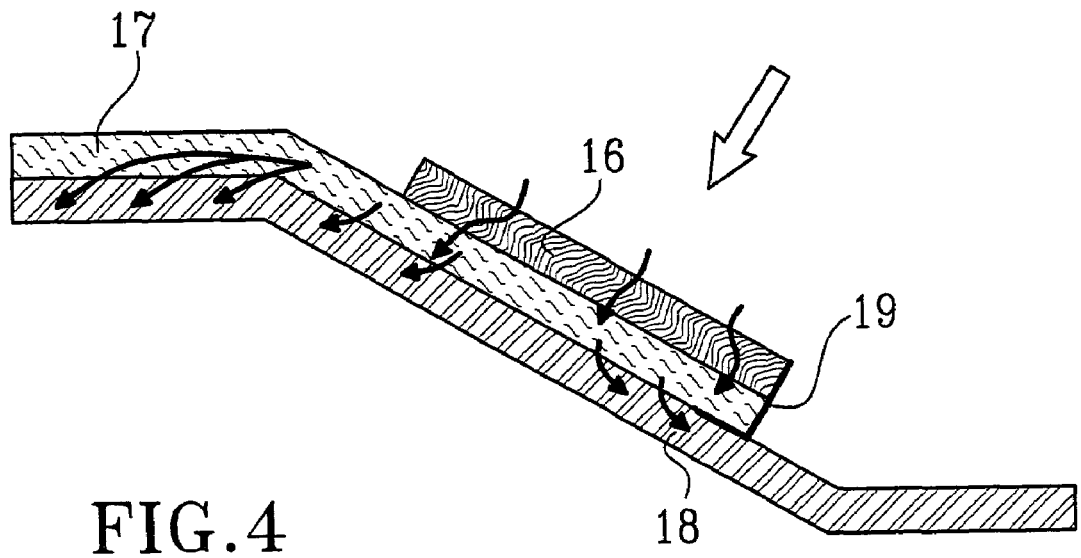
FIG. 4 illustrates the liquid distribution pattern in the absorbent body of FIG. 3a with the absorbent body in an inclined position.
Figure 5:
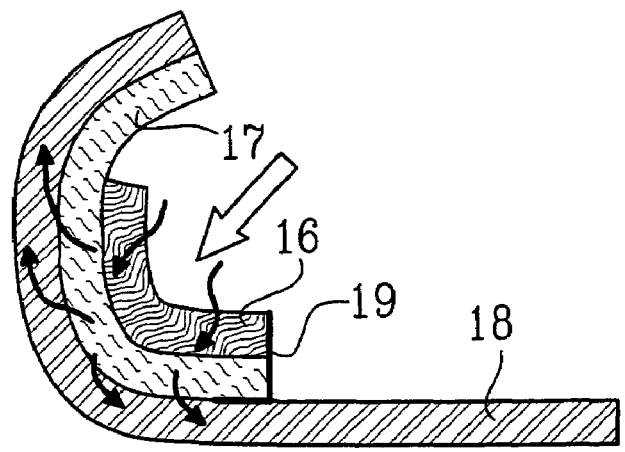
FIG. 5 illustrates the absorbent body of FIG. 3 in a position it will have on a wearer lying on the stomach.

According to the embodiment of FIGS. 3a and 4 the absorbent body comprises a fluid receiving layer 16, which during use of the article is intended to be located in the crotch area of the diaper. The material used as a receiving layer should have the ability to quickly receive large amounts of liquid, to distribute it and temporarily store it before it is absorbed by other parts of the absorbent body. A porous relatively thick receiving layer, for example in the form of a fibrous wadding, a carded fibrous web or other type of fibrous materials, has a high momentaneous liquid receiving capacity and can temporarily store liquid before it is absorbed by the absorbent body. The same applies for porous foam materials. Another example of a useful material is a layer of tow filaments, said layer may be bonded in a bonding pattern, as, e.g., disclosed in EP-A-1 035 818. Further examples of suitable materials for use as receiving layers are chemothermomechanical pulp fibers (CTMP) and crosslinked curled cellulosic fibers. The liquid is then drained successively to the underlying absorbent body, after which the receiving layer again has the capacity to receive liquid from a repeated wetting.

Underlying the fluid receiving layer 16 there is a fluid distribution layer 17, which is located in the crotch region 7 and rear region 6 of the article. The material used in the distribution layer 17 should have the ability to quickly wick fluid by capillary action along the plane of the layer. One example of a material suitable to use as a distribution layer is compressed chemical wood pulp fluff. Different types of nonwoven materials may also be used, such as spunlace materials, meltblown materials and the like.

Underlying the fluid distribution layer 17 there is a fluid storage layer 18 extending over the front, crotch and rear regions of the diaper. The material used in the storage layer 18 should have the ability to absorb and store large quantities of fluid. Suitable materials are compressed mixed or layered structure of cellulosic fluff pulp and so called superabsorbent materials, which are polymeric materials that upon fluid contact swell and bind large quantities of fluid, many times their own weight. Examples of superabsorbent materials are polyacrylates, starch and starch derivatives, carboxy alkyl cellulose material etc. Laminates of superabsorbent materials and tissue paper may also be used as storage layer.

By choosing the materials in the different layers comprised in the absorbent body in such a way that liquid transport is promoted from one layer to another layer a desired liquid distribution pattern in the article can be obtained. The liquid affinity for a certain material compared to another material is dependant on a number of factors familiar to the skilled person, for example capillary pressure, effective pore size, wetting angles, diffusion, the material's ability to chemically bind liquid in a gel etc. The international patent application WO 98/22067 describes in detail how the capillary pressure for different materials can be used to determine their mutual liquid transport properties for the purpose of producing a predetermined liquid transport pattern in an absorbent article.

In WO 00/76446 there is disclosed a method for determining the liquid transport relationships between different absorption materials, and their ability to drain liquid from each other.

To obtain optimum liquid transport in the article, it is preferable that the different parts of the absorption body are in direct contact with each other, which means that at least one surface of one absorbent part is in capillary contact with a surface of the other absorbent part, so that liquid can be transferred between the parts without the action of any other component of the absorbent body. In addition there should be no play or space between the absorption parts at the contact surfaces, at least when the parts are wet. Such a play or space interrupts the transport channels in the absorbent body. It is however possible to choose absorption materials that swell when wetted. In such a case, the absorbent material can have some play or narrow gaps between adjacent parts before wetting, on condition that said play or gaps can be bridged when the structure is wetted and swells.

Figure 3B:
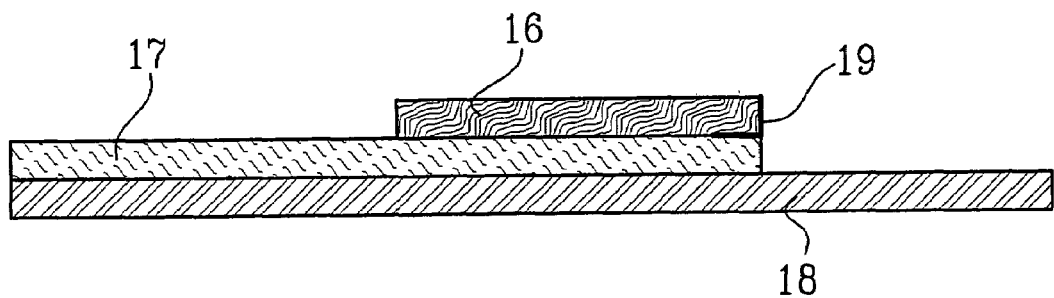
FIG. 3b is a longitudinal section through a modified embodiment of the absorbent body.

In the embodiment shown in FIGS. 3 and 4 the receiving layer 16 is in direct contact with the distribution layer 17 and the materials in these two layers should preferably be chosen so that the liquid affinity of the distribution layer 17 is higher than for the receiving layer, which means that liquid transport is promoted from the receiving layer 16 to the distribution layer 17, so that the distribution layer 17 drains liquid from the receiving layer 16.

The storage layer 18 is in direct contact with the distribution layer 17 and should preferably have a higher liquid affinity than the distribution layer 17, which means that liquid transport is promoted from the distribution layer 17 to the storage layer 18, so that the storage layer 18 drains liquid from the distribution layer 17. It is advantageous that the storage layer 18 contains superabsorbent material that can chemically bind the absorbed liquid.

A fluid barrier member 19 is according to the embodiment shown in FIGS. 3a and 4 arranged to cover the transverse front edges of the receiving and distribution layers 16 and 17 and to extend a certain distance between the distribution layer 17 and the storage layer 18. In the embodiment shown in FIG. 3b the fluid barrier member 19 is arranged to cover the transverse front edge of the receiving layer 16 and to extend a certain distance between the receiving layer 16 and the distribution layer 17.

Suitable fluid barrier materials are hydrophobic nonwoven materials, plastic films, laminates thereof or coatings of hydrophobic and/or liquid tight materials. Vapour permeable/liquid impermeable materials may advantageously be used. The fluid barrier member 19 may in an alternative embodiment be provided by melting and pressing, for example welding, together one edge portion of the fluid distribution layer 17 and/or the fluid receiving layer 16 respectively, which in this case comprises thermoplastic fibers or filaments. Thus the fluid barrier member 19 does not necessarily have to be in the form of a separate material, but may be constituted by an edge portion of the layer 16 and/or 17 that has been modified by thermal, mechanical, chemical or other treatment so as to make it prevent or at least delay liquid penetration. In an alternative embodiment the portion of the fluid barrier member 19 extending between the distribution and storage layers is excluded. Two or more fluid barrier members 19 may further be arranged at a distance from each other.

FIG. 4 illustrates the liquid distribution pattern in the absorbent body for a wearer lying on the stomach. Discharged liquid will be absorbed by the receiving layer 16 and successively drained to the distribution layer 17. Because of the distribution layer 17, which only can deliver liquid backwards in the absorbent core and the fluid barrier member 19, liquid will predominantly be spread backwards towards the rear region of the article. The distribution layer 17 will successively be drained by the underlying storage layer 18, in which the liquid can also reach the front part of the article.

In a diaper intended to be used by a person lying on the back, the absorbent core is simply reversed, so that the fluid distribution layer 17 is located in the crotch region 7 and the front region 5 of the article and the fluid barrier member 19 is arranged to cover the transverse rear edges of the receiving and distribution layers 16 and 17.

Figure 6:
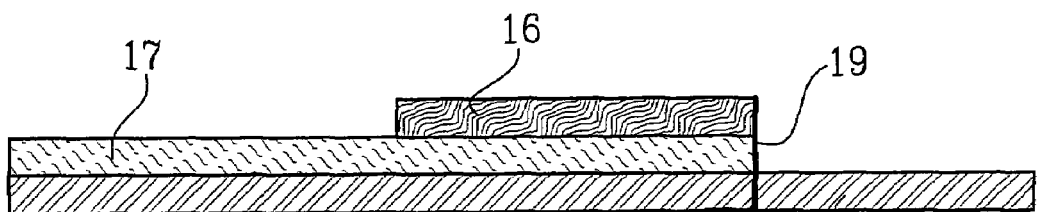
FIG. 6 is a longitudinal section through a second embodiment of an absorbent body according to the invention.

In the embodiment shown in FIG. 6 the fluid barrier member 19 also extends through the storage layer 18. This will result in a more delayed transfer of liquid to the front part of the absorbent core. In this embodiment the fluid barrier member 19 is preferably not completely liquid tight, at least not in the portion extending through the storage layer 18.

Figure 7:
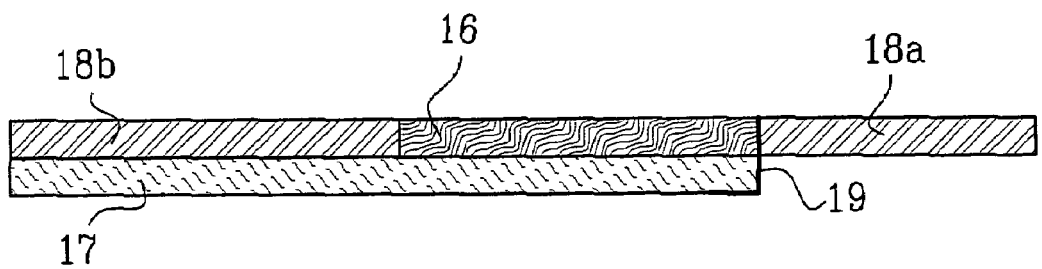
FIG. 7 is a longitudinal section through a third embodiment of an absorbent body according to the invention.

In FIG. 7 the receiving layer 16 is arranged in a recess between front and rear portions 18a and 18b of a storage layer. The receiving layer 16 may extend out to the longitudinal edges of the absorbent core, at which the front and rear storage layer portions 18a and 18b are separated from each other, or it may be arranged in a hole in the storage layer so that it is surrounded by the storage layer.

The distribution layer 17 in FIG. 7 is located below the receiving layer 16 and the rear portion of the storage layer 18b. A fluid barrier member 19 is arranged between the receiving layer 16 and the front part of the storage layer 18a and also extends down to cover the transverse front edge of the distribution layer 17.

TEST EXAMPLE

A pair of absorbent cores according to the embodiment shown in FIG. 7 were prepared. The fluid receiving layer 16 was a wetlaid thermobonded material comprising a mixture of curled crosslinked cellulosic fibers (80 weight %) and thermoplastic synthetic fibers (20 weight %). It had a basis weight of 200 g/m$^2$ and a bulk of 10 cm$^3$/g. The fluid distribution layer 17 was a dryformed layer of chemical fluff pulp having a basis weight of 200 g/m$^2$ and a bulk of 4 cm$^3$/g. The fluid storage layer 18 was a dryformed mixture of chemical fluff pulp (50 weight %) and superabsorbent material (50 weight %). It had a basis weight of 800 g/m$^2$ and a bulk of 3.5 cm$^3$/g.

One absorbent core (sample core) was provided with a fluid barrier member 19 as shown in FIG. 7. The fluid barrier member 19 was in the form of a plastic film strip. The other absorbent core (reference core) was without any fluid barrier member 19.

Figure 8:
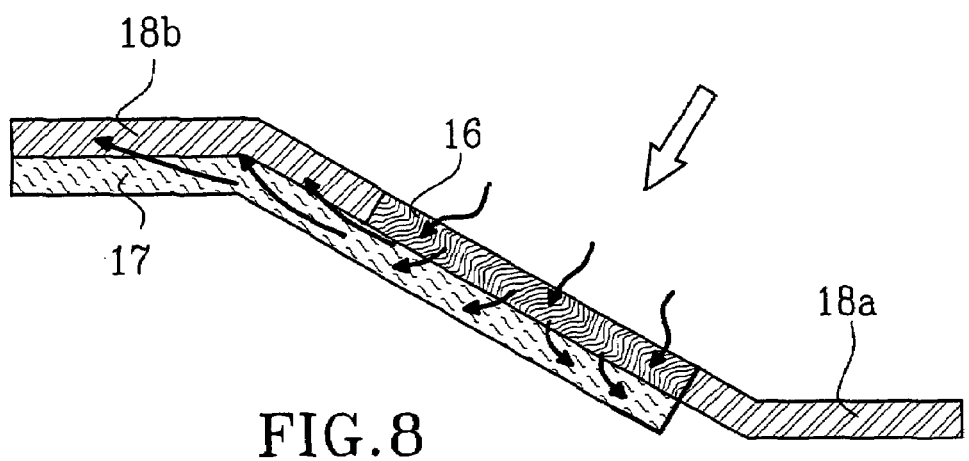
FIG. 8 illustrates the liquid distribution pattern in the absorbent body of FIG. 7 with the absorbent body in an inclined position.

The two absorbent cores were placed in a test apparatus in an inclined position as shown in FIG. 8. Three doses of synthetic urine, each of 60 ml, were added to the cores on the fluid receiving member 16 at an interval of 1 hour. The fluid distribution layer 17 and the front and rear fluid storage layers 18a and 18b were then weighed. The results are seen in the table below.

|  | Weight fluid distribution layer (g) | Weight front fluid storage layer (g) | Weight rear fluid storage layer (g) |
| --- | --- | --- | --- |
| Reference core | 50.5 | 110.8 | 43.6 |
| Sample core | 76.6 | 45.7 | 80.5 |

As is seen from these results the presence of the fluid barrier member 19 was effective in having a large part of the liquid that was absorbed by the reference core distributed into the rear fluid storage layer 18b. A major part of the distribution of liquid from the fluid receiving layer 16 to the rear liquid storage layer 18b takes place by way of the liquid distribution layer 17. Part of the liquid deposited on the fluid receiving layer 16 is transported directly to especially the front fluid storage layer 18a, and in the reference core a major amount of the liquid goes this way, while in the sample core the fluid barrier member 19 was effective in reducing this amount and instead forced the major part of the liquid to be distributed via the fluid distribution layer 17 to the rear fluid storage layer 18b. A better utilization of the available absorbent material is achieved by this, which reduces the risk for leakage.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. An absorbent article comprising:
two waist portions in the form of a front and a rear portion, and between said two waist portions a crotch portion, wherein the absorbent article has a longitudinal direction extending from one of the waist portions to the other of the waist portions, and a transverse direction that extends perpendicularly to the longitudinal direction;
an absorbent core including at least one fluid storage layer, at least one fluid distribution layer overlapping and being in fluid contact with the fluid storage layer, a fluid receiving layer being arranged in at least the crotch area of the article in direct or indirect fluid communication with the fluid distribution layer and the fluid storage layer, said fluid storage layer, said fluid distribution layer and said fluid receiving layer each having longitudinal end edges that extend along the longitudinal direction, and transverse end edges that extend along the transverse direction; and
at least one fluid barrier arranged to extend in the transverse direction of the absorbent article;
wherein the fluid distribution layer is arranged so as to extend in the crotch portion and in at least a substantial portion of one of the waist portions of the article and is absent in at least a substantial part of the opposite waist portion of the article so as to promote fluid flow from the crotch portion towards said one waist portion, and the fluid barrier is arranged at or in close proximity to one of the transverse end edges of the fluid receiving layer, the one transverse end edge being located in or adjacent the crotch portion of the article, said fluid barrier extending at least a substantial part of the thickness of said fluid receiving layer, and
at least one fluid storage layer is disposed in at least a substantial part of the front and rear portions of the article, said fluid receiving layer is disposed in at least a substantial part of the crotch and front portions of the article and is absent in at least a substantial part of the rear portion of the article and the fluid barrier is arranged at or in close proximity to the transverse end edge of the fluid receiving layer facing the rear portion of the article.

2. The absorbent article as claimed in claim 1, wherein the article is a diaper or pant diaper adapted to be used by babies lying on their stomach.

3. The absorbent article as claimed in claim 1, wherein the fluid receiving layer is arranged in a recess between front and rear portions of the fluid storage layer, the fluid distribution layer is arranged under the fluid receiving layer and the rear or the front portion of the fluid storage layer, and the fluid barrier is arranged between the fluid receiving layer and the rear or the front portion of the fluid storage layer and to substantially cover the edge of the fluid distribution layer facing the front or the rear portion of the article.

4. The absorbent article as claimed in claim 1, wherein the material in the fluid distribution layer has a higher liquid affinity than the material in the liquid receiving layer so as to promote liquid transport from the liquid receiving layer to the fluid distribution layer.

5. The absorbent article as claimed in claim 4, wherein the material in the fluid storage layer has a higher liquid affinity than the material in the fluid receiving layer and the fluid distribution layer so as to promote liquid transport from the fluid receiving layer and the fluid distribution layer to the fluid storage layer.

6. The absorbent article as claimed claim 1, wherein the fluid barrier is made from a hydrophobic nonwoven material, a plastic film material, laminates thereof, a coating of a hydrophobic or liquid tight material on a carrier material or is constituted by an edge portion of the fluid distribution layer or the fluid receiving layer respectively that has been modified by thermal, mechanical, chemical or other treatment so as to make it prevent or at least delay liquid penetration.

7. The absorbent article as claimed claim 1, wherein the absorbent article is a diaper, pant diaper, incontinence guard, or sanitary napkin.

8. The absorbent article as claimed in claim 1, wherein the fluid barrier extends parallel to the one transverse end edge.

9. An absorbent article comprising:
two waist portions in the form of a front and a rear portion, and between said two waist portions a crotch portion, wherein the absorbent article has a longitudinal direction extending from one of the waist portions to the other of the waist portions, and a transverse direction that extends perpendicularly to the longitudinal direction;
an absorbent core including at least one fluid storage layer, at least one fluid distribution layer overlapping and being in fluid contact with the fluid storage layer, a fluid receiving layer being arranged in at least the crotch area of the article in direct or indirect fluid communication with the fluid distribution layer and the fluid storage layer, said fluid storage layer, said fluid distribution layer and said fluid receiving layer each having longitudinal end edges that extend along the longitudinal direction, and transverse end edges that extend along the transverse direction; and
at least one fluid barrier arranged to extend in the transverse direction of the absorbent article;
wherein the fluid distribution layer is arranged so as to extend in the crotch portion and in at least a substantial portion of one of the waist portions of the article and is absent in at least a substantial part of the opposite waist portion of the article so as to promote fluid flow from the crotch portion towards said one waist portion, and the fluid barrier is arranged at or in close proximity to one of the transverse end edges of the fluid receiving layer, the one transverse end edge being located in or adjacent the crotch portion of the article, said fluid barrier extending at least a substantial part of the thickness of said fluid receiving layer, and
the fluid distribution layer is located between the fluid receiving layer and the fluid storage layer and the fluid barrier is arranged to extend a certain distance in between the fluid receiving layer and the fluid distribution layer.

10. An absorbent article comprising:
two waist portions in the form of a front and a rear portion, and between said two waist portions a crotch portion, wherein the absorbent article has a longitudinal direction extending from one of the waist portions to the other of the waist portions, and a transverse direction that extends perpendicularly to the longitudinal direction;
an absorbent core including at least one fluid storage layer, at least one fluid distribution layer overlapping and being in fluid contact with the fluid storage layer, a fluid receiving layer being arranged in at least the crotch area of the article in direct or indirect fluid communication with the fluid distribution layer and the fluid storage layer, said fluid storage layer, said fluid distribution layer and said fluid receiving layer each having longitudinal end edges that extend along the longitudinal direction, and transverse end edges that extend along the transverse direction; and
at least one fluid barrier arranged to extend in the transverse direction of the absorbent article;

wherein the fluid distribution layer is arranged so as to extend in the crotch portion and in at least a substantial portion of one of the waist portions of the article and is absent in at least a substantial Part of the opposite waist portion of the article so as to promote fluid flow from the crotch portion towards said one waist portion, and the fluid barrier is arranged at or in close proximity to one of the transverse end edges of the fluid receiving layer, the one transverse end edge being located in or adjacent the crotch portion of the article, said fluid barrier extending at least a substantial part of the thickness of said fluid receiving layer, the fluid barrier member is arranged also to extend at least a substantial part of the thickness of the fluid distribution layer at or in close proximity to one of the transverse end edges of said fluid distribution layer, and the fluid distribution layer is located between the fluid receiving layer and the fluid storage layer and the fluid barrier is arranged to extend a certain distance in between the fluid distribution layer and the fluid storage layer.

11. An absorbent article comprising:

two waist portions in the form of a front and a rear portion, and between said two waist portions a crotch portion, wherein the absorbent article has a longitudinal direction extending from one of the waist portions to the other of the waist portions, and a transverse direction that extends perpendicularly to the longitudinal direction;

an absorbent core including at least one fluid storage layer, at least one fluid distribution layer overlapping and being in fluid contact with the fluid storage layer, a fluid receiving layer being arranged in at least the crotch area of the article in direct or indirect fluid communication with the fluid distribution layer and the fluid storage layer, said fluid storage layer, said fluid distribution layer and said fluid receiving layer each having longitudinal end edges that extend along the longitudinal direction, and transverse end edges that extend along the transverse direction; and at least one fluid barrier arranged to extend in the transverse direction of the absorbent article;

wherein the fluid distribution layer is arranged so as to extend in the crotch portion and in at least a substantial portion of one of the waist portions of the article and is absent in at least a substantial part of the opposite waist portion of the article so as to promote fluid flow from the crotch portion towards said one waist portion, and the fluid barrier is arranged at or in close proximity to one of the transverse end edges of the fluid receiving layer, the one transverse end edge being located in or adjacent the crotch portion of the article, said fluid barrier extending at least a substantial part of the thickness of said fluid receiving layer, the fluid barrier member is arranged also to extend at least a substantial part of the thickness of the fluid distribution layer at or in close proximity to one of the transverse end edges of said fluid distribution layer, and the fluid distribution layer is located between the fluid receiving layer and the fluid storage layer and the fluid barrier is arranged to extend also through the fluid storage layer.

12. An absorbent article comprising:

two waist portions in the form of a front and a rear portion, and between said two waist portions a crotch portion, wherein the absorbent article has a longitudinal direction extending from one of the waist portions to the other of the waist portions, and a transverse direction that extends perpendicularly to the longitudinal direction;

an absorbent core including at least one fluid storage layer, at least one fluid distribution layer overlapping and being in fluid contact with the fluid storage layer, a fluid receiving layer being arranged in at least the crotch area of the article in direct or indirect fluid contact with the fluid distribution layer and the fluid storage layer, said fluid storage layer, said fluid distribution layer and said fluid receiving layer each having longitudinal end edges that extend along the longitudinal direction, and transverse end edges that extend along the transverse direction;

the fluid distribution layer being in direct fluid communication with the fluid receiving layer and the fluid storage layer;

at least one fluid barrier arranged to extend in the transverse direction of the absorbent article;

wherein the fluid distribution layer is arranged so as to extend in the crotch portion and in at least a substantial portion of one of the waist portions of the article and is absent in at least a substantial part of the opposite waist portion of the article so as to promote fluid flow from the crotch portion towards said one waist portion, and the fluid barrier is arranged at or in close proximity to one of the transverse end edges of the fluid receiving layer, the one transverse end edge being located in or adjacent the crotch portion of the article, said fluid barrier extending at least a substantial part of the thickness of said fluid receiving layer.

13. The absorbent article as claimed in claim 12, wherein the liquid affinity of the fluid distribution layer is higher than the liquid affinity of the fluid receiving layer, and the liquid affinity of the fluid storage layer is higher than the liquid affinity of the fluid distribution layer.

* * * * *